United States Patent [19]

Schilling et al.

[11] Patent Number: 5,034,060
[45] Date of Patent: Jul. 23, 1991

[54] CATIONIC AQUEOUS BITUMINOUS EMULSION-AGGREGATE SLURRIES WITH IMPROVED CURING RATES

[75] Inventors: Peter Schilling; Hans G. Schreuders, both of Charleston, S.C.

[73] Assignee: Westvaco Corporation, New York, N.Y.

[21] Appl. No.: 312,824

[22] Filed: Feb. 21, 1989

[51] Int. Cl.$^5$ .................. C08L 95/00; B01J 13/00
[52] U.S. Cl. .................. 106/277; 106/273.1; 106/283; 252/311.5; 252/357
[58] Field of Search .......... 252/311.5, 351, 357; 106/273.1, 277, 283

[56] References Cited

U.S. PATENT DOCUMENTS

| | | | |
|---|---|---|---|
| 3,575,883 | 4/1971 | Foley | 252/354 |
| 4,447,269 | 5/1984 | Schreuders et al. | 106/277 |
| 4,450,011 | 5/1984 | Schilling et al. | 106/269 |
| 4,462,840 | 7/1984 | Schilling et al. | 106/277 |
| 4,464,286 | 8/1984 | Schilling | 252/311.5 |
| 4,478,642 | 10/1984 | Schilling et al. | 106/277 |
| 4,494,992 | 1/1985 | Schilling et al. | 252/311.5 X |
| 4,547,224 | 10/1985 | Schilling | 106/273 |
| 4,597,799 | 7/1986 | Schilling | 252/311.5 X |
| 4,639,273 | 1/1987 | Gilmore et al. | 208/44 X |
| 4,658,036 | 4/1987 | Schilling | 564/153 X |
| 4,676,927 | 6/1987 | Schilling et al. | 252/311.5 |
| 4,957,560 | 9/1990 | Schilling | 252/311.5 X |

OTHER PUBLICATIONS

Sax et al., *Hawley's Condensed Chemical Dictionary*, 11th Ed. (New York, Van Nostrand Reinhold Co., 1987), pp. 34–35.

*Primary Examiner*—Richard D. Lovering
*Assistant Examiner*—Daniel S. Metzmaier
*Attorney, Agent, or Firm*—Terry B. McDaniel; Daniel B. Reece, IV; Richard L. Schmalz

[57] ABSTRACT

Slurries are formed with cationic emulsions prepared by emulsifying bitumen, such as an asphalt, in water with a cation-active emulsifier which is the product of the reaction of polyamine with certain polycarboxylic acids, which product is subsequently modified by reaction with from 10–30% of a member of the group consisting of acetic anhydride, phthalic anhydride, propylene carbonate, and styrene oxide.

6 Claims, No Drawings

CATIONIC AQUEOUS BITUMINOUS EMULSION-AGGREGATE SLURRIES WITH IMPROVED CURING RATES

BACKGROUND OF THE INVENTION

(1) Field of the Invention

The present invention relates to mixing-grade, quick-setting cationic aqueous bituminous emulsion-aggregate paving slurry seal mixtures. More particularly, this invention relates to slurries formed with cationic emulsions prepared by emulsifying bitumen, such as an asphalt, in water with a cation-active emulsifier which is the product of the reaction of modified polyamine with certain polycarboxylic acids. Most particularly, this invention relates to the employment of these cation-active emulsifiers which have been post-reacted with from 10-30% of a member of the group consisting of acetic anhydride, phthalic anhydride, propylene carbonate, and styrene oxide.

(2) Description of the Prior Art

Conventionally, emulsion slurry seals are formulated from (1) mineral aggregate which is a fine stone aggregate and/or mineral filler and (2) about 15% to about 25% by weight thereof of a mixing-grade, quick-setting or slow-setting emulsion containing from about 50% to about 75% by weight of bituminous residue (usually asphalt), with a further addition of about 5% to about 25% of water, based on the weight of the dry aggregate, to attain slurry consistency. Usually, densely-graded aggregates, such as granite screenings, limestone screenings, dolomite screenings and blast furnace slag, are combined with bituminous emulsions to produce slurry seal compositions. These aggregates range in size from anything passing all through a sieve of No. 4, and even No. 10 mesh, with from 15% to 20% passing through as fine a mesh as 200 mesh, as described in ASTM C136.

The advent of slurry seal as a paving and road maintenance technique was first developed for use with anionic aqueous bituminous emulsions. A slurry seal is an intimate mixture of emulsified bituminous material and fine-grained aggregate held in suitable suspension until applied to the road surface. The slurry seal emulsion must be of an oil-in-water type. In such a mixture with aggregate, the aqueous emulsion form of the bituminous material has been generally preferred because it is less hazardous and more economical to use than hot mix or cutback (solvent containing) asphalts. Further, the aqueous emulsion form can be stored, transported and applied at much lower temperatures, obviating the necessity of heating equipment to maintain a bitumen-aggregate system in a workable or usable form. While these advances have been recognized, widespread acceptance has not been achieved due to disadvantages found in previous aqueous bituminous emulsions.

More recently, cationic bituminous emulsions have come into use and eliminate many of the disadvantages of the anionic emulsions. Bituminous emulsions formulated using cationic emulsifiers do not "break" in the same manner as anionic emulsions, but rather the bituminous material is deposited from the emulsion due to the attraction of polar charges between the positively charged bituminous droplets and negatively charged aggregate surfaces. Thus, cationic bituminous emulsions deposit more rapidly than the anionic bituminous emulsions on aggregate surfaces and are bonded to the aggregate by the electrostatic action at the interface of the bitumen and the aggregate material.

The aqueous cationic bituminous emulsions themselves are relatively stable, and the emulsion stability may be enhanced by various additives well known in the art. Most cationic bituminous emulsions, however, deposit on the surface of aggregate materials rapidly when aggregate is contacted with the emulsions. Bitumen from an aqueous cationic bituminous emulsion is deposited from the emulsion due to the charge attraction between the bituminous droplets and the aggregate materials. The rapid setting action of cationic bituminous emulsions is of considerable advantage in road building, such as seal coats, since the roads can be opened to traffic shortly after application of the coating. Although the rate of asphalt deposition, for example, from the emulsion can be controlled to some extent, the time required for complete deposition is never very long and it is therefore the practice to combine the cationic emulsion with the aggregate at the site of road construction, either on the surface of the road itself, or in a mobile mixer which permits the emulsion aggregate mix to be rapidly spread. Due to the charge attraction mechanism, the rapidity of deposition of bituminous materials from the cationic emulsion is closely related to the generally negatively charged surface area of the aggregate or filler material. Thus, while a specific cationic bituminous emulsion might provide suitable properties for use in conjunction with some aggregates, the same cationic emulsion may not exhibit suitable properties when used with very finely ground materials having vastly larger total surface area. The rapid deposition characteristics of the cationic bituminous emulsions frequently makes it impossible to use such emulsions with fine-grained aggregate in slurry form such as in gun application or spreader box application. Therefore, since the slurry seal should mix well, pump well, lay down well, not stiffen while being applied, and, after setting, wear well under traffic, it is particularly desirable to be able to control the setting time of the slurry for various aggregates employed.

Acidified reaction products of the above described polycarboxylic acids, anhydrides, sulfonated fatty acids and epoxidized glycerides with certain polyamines are suitable emulsifiers yielding asphalt emulsions which can be mixed with fine grained aggregate to give workable aggregate/emulsion mixes.

These types of emulsifiers are disclosed in U.S. Pat. No. 4,447,269 to Schreuders et al., U.S. Pat. No. 4,450,011 to Schilling et al., U.S. Pat. No. 4,547,224 to Schilling et al., U.S. Pat. No. 4,462,840 to Schilling et al., U.S. Pat. No. 464,286 to Schilling, U.S. Pat. No. 4,561,901 to Schilling, U.S. Pat. No. 4,597,799 to Schilling, and U.S. Pat. No. 4,676,927 to Schilling et al.

However, cationic emulsions produced with these emulsifiers can in many cases only be mixed with the aggregate in the presence of inorganic blending agents such as Portland cement or hydrated lime. These additives are generally employed at a dosage of 0.5-3% based on the weight of the aggregate. The addition of these blending agents has the effect of causing the aggregate/emulsion mix to cure slower, specifically at temperatures below 75° F. Mix and cure behavior is dependent on the type of aggregate and source of the asphalt.

Accordingly, an object of this invention is to provide novel emulsifiers which produce cationic emulsions which can be mixed with aggregate and provide faster curing asphalt/aggregate matrixes at lower temperatures (60°-75° F.) even in the presence of blending agents.

A further object of this invention is to provide a novel mixture of aggregate and bituminous emulsion.

An additional object is to provide a mixture of the above character which is workable under a broad range of conditions.

Another object is to provide a mixture of cationic bituminous emulsion and aggregate with variable setting time.

A particular object is to provide an aqueous bituminous emulsion and fine-grained aggregate slurry mixture which deposits at a fairly rapid rate after being applied to the surface to be treated, and is usable for a longer period of time to enable application in slurry form.

SUMMARY OF THE INVENTION

The above objectives are met in the cationic aqueous bituminous emulsion-aggregate slurries formed with cationic emulsions prepared by emulsifying bitumen, such as an asphalt, in water with a cation-active emulsifier which is a modified product of the reaction of a polyalkylene polyamine with a member selected from the group consisting of polycarboxylic acids and anhydrides of the following general formulae

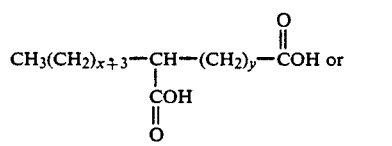

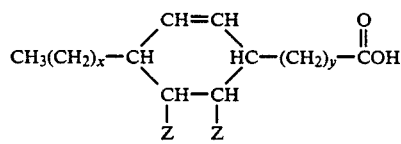

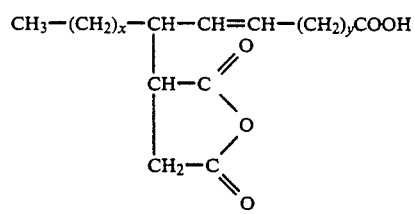

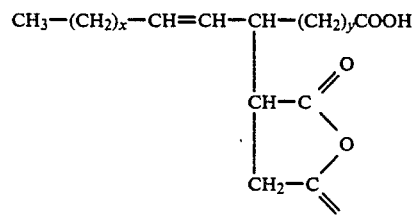

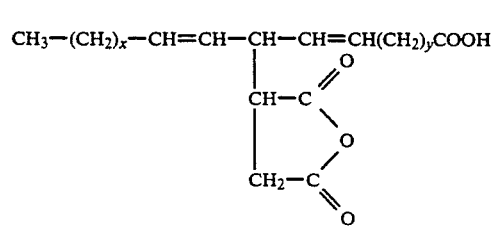

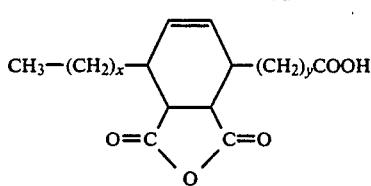

wherein x and y are integers from 3 to 9, x and y together equal 10-14, at least one Z is a carboxylic acid group and any remaining Z is hydrogen. The amine condensates are modified by reaction with an aliphatic $C_1$-$C_{20}$ mono-, di- or tricarboxylic acid, its corresponding anhydride, such as acetic anhydride, an aromatic mono- or dicarboxylic acid or its corresponding anhydrides, such as phthalic anhydride. Other modifications are the reaction of the intermediate amidoamines or imidazolines with organic carbonates such as propylene carbonate, and with epoxides such as styrene oxide.

DESCRIPTION OF THE PREFERRED EMBODIMENTS p A typical cationic aqueous bituminous emulsion aggregate slurry is formulated in the laboratory with an amount of aggregate to which up to 3% Portland cement or hydrated lime may have been added, pre-wetted with water and mixed with a suitable cationic bituminous emulsion to a desired consistency.

Suitable consistency is obtained by using mixed gradations of aggregates forming a smooth non-separating uniform mixture of cationic aqueous bituminous emulsion-aggregate which can be evenly spread onto an existing surface. The ultimate toughness of the applied slurry is obtained as the bitumen, such as asphalt, deposits on the aggregate particles and binds the newly applied coating to the pre-existing surface as a mixture of asphalt cement and aggregate.

As a paving technique at the roadsite, a mobile self-propelled unit capable of uniformly metering the aggregate, water, inorganic or organic additive and emulsion components may be used. A typical unit is equipped with separate tanks for aggregate, water, additive and emulsion which are continually metered into a mixing chamber at a pre-determined ratio. The continually fed components are retained in the mixing chamber for approximately one minute and then fed into a spreader box and applied to the surface to be coated. Batch operated pneumatic devices can also be used for suitable placement of the cationic bituminous aggregate slurries of this invention.

The slurry of this invention broadly comprises aggregate and a bituminous emulsion made up of bitumen, water and, as cationic emulsifier, the invention modified reaction product of a polyalkylene amine and a polycarboxylic acid as described above.

Suitable emulsifiers are also obtained when the polyalkylene amines are condensed with reaction products of animal fats and vegetable oils and fumaric acid, maleic anhydride, acrylic acid or methacrylic acid or the epoxidized derivatives of soybean oil, linseed oil, or esters such as alkyl oleates or alkyl tallates or animal fats obtained by epoxidation with peracetic acid or perbenzoic acid and post-treated with the reactants listed earlier. These oxiranes are most widely used as plasticizers and stabilizers for polyvinyl chloride or as coreactants for epoxy resins. Epoxy acids or esters can also be derived from fatty chlorohydroxy acids or esters. As an example, the expoxidized triglyceride of oleic acid may be used to describe an ingredient of the emulsifiers of the invention:

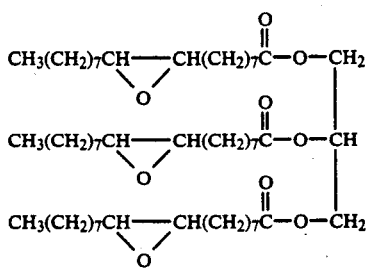

Unlike the polyamidoamine emulsifiers disclosed in the prior art, the invention modified polyamidoamines are obtained by reacting polyamidoamines or imidazolines with reactants such as (1) aliphatic or cycloaliphatic $C_1$-$C_{30}$ monocarboxylic acids, $C_2$-$C_{30}$ dicarboxylic acids, $C_3$-$C_{30}$ tricarboxylic acids, aromatic mono-, di- and tricarboxylic acids or the corresponding aliphatic or aromatic anhydrides, (2) alkyl-carbonates with noncyclic structures such as dimethyl or diethyl carbonate or with cyclic structures such as ethylene- or propylene carbonate, (3) reactive epoxides such as ethylene oxide, propylene oxide or styrene oxide.

Upon heating of a polyamine such as diethylene triamine with the $C_{21}$-dicarboxylic acid, or $C_{22}$-tricarboxylic acid anhydride, which is used as general examples, to 230°-250° C., polyamidoamines or polyimidoamidoamines are formed as follows:

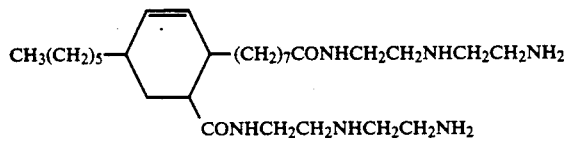

or

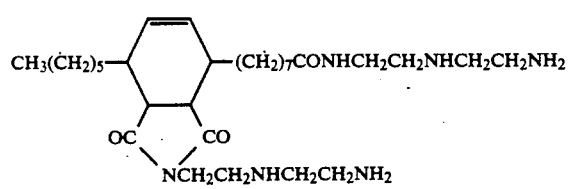

These products are, however, never obtained in high purity, since the reaction of two moles polyamine with one mole reactive acid is rather complex and some unreacted amine and higher molecular weight polyamino amides are formed as by-products.

Polyamines suitable as precursors are those which are able to form imidazolines or amidoamines with carboxylic acids such as ethylene diamine, diethylene triamine, triethylene tetramine, tetraethylene pentamine, pentaethylene hexamine, and higher homologues; N-aminoethyl propane diamine, N,N'-diaminoethyl propane diamine and the N-aminoethyl- or N,N'-diaminoethyl-substituted butane diamines, pentane diamines and hexane diamines, and N-hydroxy ethyl ethylene diamine. These compounds have the general formula $H_2NCH_2CH_2NHR$ R=H—, $CH_3$—, $C_2H_5$—, $C_3H_7$—, —$CH_2CH_2OH$, —$(CH_2CH_2NH)_xH$ x=1, 2, 3, 4, ... 10 or, $R_1R_2N(CH_2)_yNHR_3$ $R_1$=H—, $CH_3$—, $C_2H_5$—, $C_3H_7$—, $NH_2CH_2CH_2$—,
$R_2$=H—, $CH_3$—, $C_2H_5$—,
$R_3$=H—, $CH_3$—, $C_2H_5$—, $C_3H_7$—, $NH_2CH_2CH_2$—,
y=2, 3, 4, 5, 6.

Amines capable of forming amidoamines but not imidazolines are: 1,3-diaminopropane, 1,4-diaminobutane, 1,5-diaminopentane, 1,6-diaminohexane, piperazine (1,4-diazacyclohexane), N-aminoethylpiperazine, N-hydroxyethyl piperazine, N-aminopropyl-propane diamine-1,3, N-methyl-N-aminopropylpropane diamine-1,3, N-aminohexylhexane diamine-1,6.

In addition, polyamines containing other functionalities such as (—O—), thioether (—S—), sulfoxide (—SO—) sulfone (—$SO_2$—) groups, as well as aromatic structures are also suitable for condensation.

$R_1HN(CH_2)_xY(CH_2)_zNH_2$
Y=O, S, SO, $SO_2$, $C_6H_4$
x=2-10
z=2-10

Further modifications are carried out by cooling the intermediate amine condensates to about 150° C. and after addition of the reactants reheating of the mixture to 220° C.-250° C.

The reaction products with acetic anhydride, phthalic anhydride, propylene carbonate and styrene oxide may serve as examples. The reaction can occur on any primary and secondary amino group resulting in N-acyl and N-hydroxyalkyl and N-alkyl derivatives. When carbonates, diepoxides, epichlorohydrin or polycarboxylic acids are employed, the molecular weight of the amidoamines is increased by crosslinking reactions.

The following compounds may serve as general examples for these reactions.

Up to two moles acetic anhydride (four moles acetic acid equivalents) can be reacted. The amount used for the aggregate mixes. The higher the amount of modifying agent used, the faster the rate of cure. However, unreacted NH- or $NH_2$-groups have to be conserved for protonation to form the cationic soap.

Reaction with acetic anhydride (1 mole):

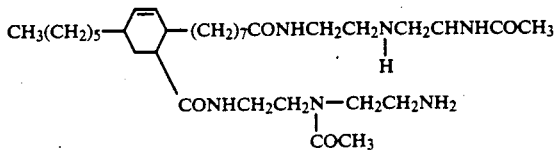

Reaction with phthalic anhydride (1 mole):

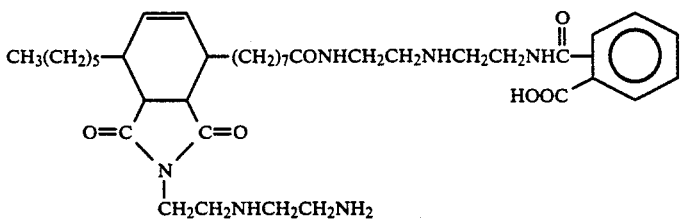

Reaction with propylene carbonate (1 mole):

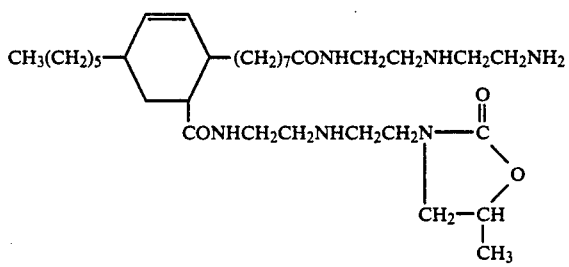

The cyclic urethane intermediate will undergo further crosslinking reaction yielding urea derivatives.

Reaction with sytrene oxide (1 mole):

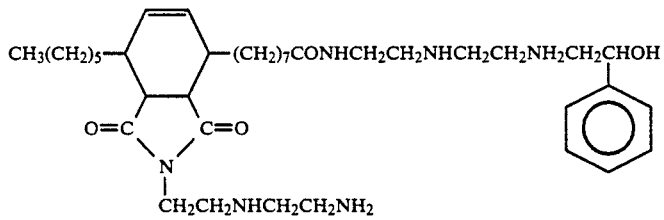

These modifications of the reaction products of polyethylene amines with the above described $C_{19}$-, $C_{21}$-, $C_{22}$-polycarboxylic acid and anhydrides and the blends of these complex polycarboxylic acids or anhydrides with $C_8$–$C_{18}$ fatty acids as asphalts emulsifiers, and specifically as emulsifiers for solventless asphalt emulsions and emulsions for slurry seal applications, were heretofore unknown.

The examples which follow are illustrative of emulsifiers used to obtain cationic asphalt in water emulsions eminently useful for mixing under shear with a variety of siliceous and calcareous aggregates. After setting (evaporation of water), the asphalt films show excellent adhesion to the aggregate surface.

In preparing the bituminous emulsions employed in the invention paving slurry seal mixtures, an aqueous acidic solution of the emulsifiers described below is intimately mixed under high shear in a colloid mill. The bitumen content can range from 30% to about 80% by weight, preferably between 60% and 70%. The dosage of the emulsifier can range from 0.1-10% by weight of the emulsion, preferably between 0.5-2% by weight of the emulsion. Dependent on the emulsifier, a slurry grade emulsion is obtained in a pH range of 1-7, with the optimum performance at a pH of about 1.5-2.5.

The "bitumen" used in the emulsion may be derived from domestic or foreign crude oil: it also includes bitumen, natural asphalt, petroleum oil, oil residue of paving grade, plastic residue from coal tar distillation, petroleum pitch, and asphalt cements diluted from solvents (cutback asphalts). Practically any viscosity or penetration graded asphalt cement for use in pavement construction as described in ASTM designation D-3381 and D-946 may be emulsified with the aid of the emulsifiers of this invention.

The cationic soap solutions are normally obtained by suspending the modified amidoamine or imidazoline in water to which a sufficient amount of a suitable acid, for instance, hydrochloric, sulfuric, and phosphoric acid or the like is added until the desired pH value below 7 is reached and a clear emulsifier solution is obtained. Thereafter, the soap solution which is preheated to 55° C. and the fluid asphalt which is preheated to 120°-125° C. are mixed under high shear in a colloid mill to testing according to ASTM D-244, the emulsions are stored at 70° C. for 16 hours.

The aggregates of the invention paving slurry seal mixtures are densely graded aggregates which range in size from anything passing through a No. 4 sieve and at least 80% retained on 200 mesh.

Aggregate mixing tests are performed by mixing the aggregate with water and aqueous bituminous emulsion. An inorganic additive-mineral filler, such as portland cement, hydrated lime, limestone dust and fly ash, may be added to accelerate set/break time and organic salts, such as ammonium sulfate, or emulsifiers may be added to retard the set/break of the slurry system. Such additives shall comply with the requirements of ASTM D-242. The materials are mixed in a mixing bowl until a homogeneous slurry mixture is obtained. The inability to form a stable slurry within 3 to 4 minutes of mixing time when proper proportions of each ingredient are used would indicate a mixture in which the materials are not compatible. This mix design is necessary to simulate field conditions. After the slurry is mixed, it is spread in a mold which is placed on an asphalt felt, and the set/break time is measured by blotting the exposed slurry surface with a paper towel. The slurry is considered to be "set" when no stain is transferred to the towel. The cure time could also be measured with a cohesion testing device. Many other tests such as described in ASTM D-3910 are used to measure strength and other physical properties of slurry. The Performance Guide for Slurry Seal published by the Asphalt Emulsion Manufacturers Association is used to measure the performance of the slurry seal.

The emulsion should be stable during mixing and should set within the designed time period following application. The emulsifiers of this invention perform very satisfactorily without auxiliary emulsifiers. For instance, the setting times can be controlled with the concentration of emulsifier, the addition of lime, cement or other inorganic additive or an organic additive, which would alter the break characteristics of the slurry system. An organic additive-polymer latex may also be employed to strengthen the matrix. The organic additive is preferably added to the emulsion-aggregate slurry.

Either a mixture of tall oil fatty acids, preferably tall oil pitch, can be added to the bitumen (asphalt) prior to emulsification to control break time or improve the viscosity of the emulsion, or blends of the above described amidoamines with compatible cationic or nonionic emulsifiers may be used for the emulsification of the bitumen. Auxiliary emulsifiers, which may constitute up to 90% of the total combined emulsifier formulation, are fatty amines, fatty propane diamines, fatty amidoamines, and fatty imidazolines. Others are fatty monoquaternary ammonium salts and fatty diquaternary diammonium salts and nonionic emulsifiers, such as ethylene glycol polyethers of nonyl- or dodecyl phenol. Combinations of modified amidoamines based on fatty monocarboxylic acids, of various sources and the $C_{19}$- and $C_{21}$-dicarboxylic acids or $C_{22}$-tricarboxylic acid or anhydrides disclosed in this invention can also be obtained by first reacting polyamines with a blend of fatty monocarboxylic acids and di- or tricarboxylic acids or anhydrides and further reacted with carbonates, epoxides and acetic or phthalic anhydride as described above. Monocarboxylic acids suitable for this purpose are tall oil fatty acids, crude tall oil, rosin acids, tall oil pitch, tallow fatty acids, soya fatty acids and the like. Kraft lignin, oxidized lignin, desulfonated sulfite lignin or Vinsol (a wood rosin based oxidation product) may also be co-reacted.

Dimer acids, which are long chain $C_{36}$-aliphatic carboxylic acids obtained by dimerization of fatty acids of acid is produced by Emery Industries, Inc. under the trade name "Empol ® Dimer Acids."

In a similar way, blends of sulfonated fatty acids as well as fumarized or maleinized rosin (resin acids) or epoxidized glycerides or other esters, with the above described co-reactants (fatty acids, oils, fats, lignins, Vinsol, dimer acid) can be reacted with the modified polyamines to give combinations of polyaminoamidoamines.

The emulsions prepared with these polyaminoamide condensates disclosed in this invention are stable and can be stored for a long period of time until required for use. The cationic aqueous bituminous emulsions employed in the invention slurries are quick-setting, mixing grade slurries under ASTM D-2397.

The practice of this invention may be seen in the following examples wherein the preparation of various types of slurries of the invention is described.

EXAMPLE 1

The following variety of emulsifiers were prepared for emulsion-aggregate slurry testing.

Emulsifier A

A one-liter three-necked flask equipped with stirrer, condenser, Dean Stark trap, thermometer and dropping funnel was charged with 130 grams of $C_{21}$-dicarboxylic acid (DIACID 1550 ®). With good stirring 100 grams of a polyethylene amine blend with an average molecular weight of 140 were added slowly and heated to 240° C. for 30 minutes. The water of condensation was collected in the Dean Stark trap.

Emulsifier B

Two hundred grams of Emulsifier A were cooled to 150° C., and through a dropping funnel 20 grams of acetic anhydride were added slowly with stirring. The reaction mixture was heated to 220° C. for one hour and cooled for discharge. The addition of solvents such as isopropanol or ethylene glycol to obtain a fluid product is optional.

Emulsifier C

A one-liter three-necked flask equipped with stirrer, condenser, Dean Stark trap, thermometer and dropping funnel was charged with 150 grams of a 40:60 blend of a $C_{22}$-tricarboxylic acid and tall oil fatty acids containing about 5% resin acids and heated to 50° C. To this, 150 grams of a polyethylene amine blend with an average molecular weight of 140 were added slowly and heated to 220° C. for one hour. The distillate was collected in the Dean Stark trap.

Emulsifier D

Two hundred grams of Emulsifier C were cooled to 130° C., and with stirring 20 grams of acetic anhydride were introduced slowly through a dropping funnel. It was heated to 220° C. for one hour.

Emulsifier E

Two hundred grams of Emulsifier C were cooled to 120° C., and 20 grams styrene oxide were added slowly. The mixture was heated to 230° C. for one hour.

Emulsifier F

Two hundred grams of Emulsifier C were cooled to 120° C., and 20 grams of propylene carbonate were added dropwise. The reaction mixture was heated to 230° C. for 30 minutes.

Emulsifier G

Two hundred grams of Emulsifier C were cooled to 120° C., and 30 grams of phthalic anhydride were added in small portions. The reaction mixture was heated to 220° C. for one hour.

Emulsifier H

Two hundred fifty grams of a 40:60 blend of $C_{22}$-tricarboxylic acid and tall oil fatty acids and 100 grams of a polyethylene amine blend with an average molecular weight of 140 were blended slowly at 150° C. and heated to 220° C. After all the distillate was collected, it was cooled and discharged.

Emulsifier I

One hundred grams of Emulsifier H were heated to 120° C., and 10 grams of acetic anhydride were added slowly with stirring. It was heated to 230° C. for 30 minutes.

Emulsifier J

This emulsifier was prepared by reacting 200 grams of Emulsifier H with 20 grams of phthalic anhydride at 220° C. Procedure is described under Emulsifier G.

One hundred grams of Emulsifier H were heated to 120° C., and five grams of fumaric acid were introduced slowly. It was heated to 220° C. for 30 minutes.

EXAMPLE 2

A cationic aqueous bituminous emulsion was prepared employing each of the emulsifiers of Example 1 and aggregate mixing tests were performed with each emulsion as previously described.

First, cationic aqueous bituminous emulsions were prepared with 64% Exxon asphalt (penetration value of 125/150) at 60° C., 1.5% emulsifier at pH 2.0 and water to make up 100% (percentages based on the weight of the emulsion).

Next, slurries were prepared by adding to one hundred grams of Camak aggregate (granite screenings) 12% of the cationic aqueous bituminous emulsion, 10-14% water and either 0% or 2% portland cement as mixing aid (percentages based on the weight of the aggregate) and mixing in a bowl for 30 seconds.

For all improved emulsifiers tested, stable homogeneous slurry mixtures were achieved within 30 seconds of mixing time.

EXAMPLE 3

This example illustrates the curing behavior of the slurries prepared in Example 2.

The slurry curing time was determined with means of a modified ASTM D-3910 cohesive strength tester. The modified cohesive tester consists essentially of (1) a frame, (2) instrument panel, (3) pressure gauge, (4) pressure regulator, (5) 4-way air valve and (6) a double-rod air cylinder mounted vertically so that a (7) rubber faced foot when lowered by air pressure against a specimen may be manually twisted to failure by a (8) peak-reading torque wrench.

Specimens are prepared and cast in a 60 mm diameter mold. A 6 mm-deep mold is used for aggregates 100% passing the 4.75 mm (#4 or 3/16") sieve and a 10 mm-deep mold is used for aggregates 100% passing the 8 mm (5/16") sieve. The specimens are cast on 10 cm (4") squares of non-absorptive 16-pound bitumen saturated roofing felt. This felt has been used for specimen mountings of all the data presented in this paper.

The modified cohesion tester is similar to the Armak ASTM D-3910-80 machine except that it is designed for a constant regulated air supply, convenient 4-way cylinder valve to operate the cylinder at controlled rate of speed. The cylinder is larger and more rugged. The contact foot used here is a flat ¼ neoprene disc of 50–60 durometer hardness, 1-18" diameter rather than a 1" diameter plug cut from an automobile tire. The procedures used may be found in Appendix A (ISSA Technical Bulletin TB #139 12/82). The pressure exerted on the foot is 92.3% of the gauge reading. The test pressure is set at 200 kPa (28.44 psi) and the cylinder foot is lowered against the centered specimen and allowed to compact the specimen for 5 to 6 seconds. The torque meter is placed on the upper cylinder rod end and twisted by hand in a firm smooth horizontal motion through 90° to 120° of arc within .7 to 1.0 second. The maximum torque pointer is read and the results recorded, the foot raised and cleaned and torque pointer is reset.

A series of specimens are prepared by casting a fresh mixture into 6 mm diameter rings 6 or 10 mm thick and centered on a non-absorbent surface such as 10 cm squared of 15-pound saturating roofing felt. The number of data points during a specified time span determines, of course, the number of specimens and amount of mix required.

Peak torques are recorded at 15, 30, 60, 90 minutes and so on.

TABLE

Emulsion: Exxon 120/150 Penetration Asphalt, pH 2.0, 1.5% Emulsifier
Aggregate: Granite (Camak) 2% Portland Cement
CURING TIMES OF SLURRY SEAL MIXES

| Emulsifier | Cohesive Strength (kg × cm) After | | | |
|---|---|---|---|---|
| | 30 | 45 | 60 | 90 |
| | (min.) | | | |
| Emulsifier A (control) | 12.1 | 12.7 | 13.8 | 13.6 |
| Emulsifier B | 11.2 | 12.2 | 14.6 | 20+ |
| Emulsifier C (control) | 11.1 | 13.8 | 13.6 | 14.5 |
| Emulsifier D | 14.4 | 16.6 | 16.4 | 20+ |
| Emulsifier E | 14.1 | 15.3 | 17.9 | 20+ |
| Emulsifier F | 15.2 | 14.4 | 18.8 | 20+ |
| Emulsifier G | 15.6 | 16.8 | 20+ | 20+ |
| Emulsifier H (control) | 15.6 | 12.7 | 13.8 | 13.6 |
| Emulsifier I | 11.5 | 13.1 | 16.6 | 20+ |
| Emulsifier J | 16.7 | 16.3 | 17.1 | 20+ |
| Emulsifier K | 11.0 | 15.7 | 15.0 | 16.1 |

This example shows that slurries containing the invention emulsifiers cure faster than the slurries containing the non-modified emulsifiers. Twenty kg×cm cohesive strength is necessary for re-opening the new road surface to rolling traffic.

While the invention as been described and illustrated herein by reference to various specific materials, procedures and examples, it is understood that the invention is not restricted to the particular materials, combinations of materials, and procedures selected for that purpose. Numerous variations of such details can be employed, as will be appreciated by those skilled in the art.

What is claimed is:

1. In a cationic aqueous bituminous emulsion-aggregate slurry formed with cationic emulsions prepared by emulsifying bitumen in water with a cation-active emulsifier which is an amine condensate product of the reaction at a temperature of from about 30° C. to about 250° C., of about 2 moles of a polyalkylene amine with about 1 mole of a member selected from the group consisting of polycarboxylic acids and anhydrides of the following general formulae

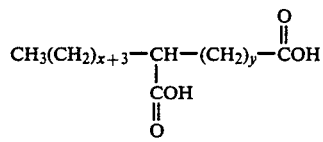

or

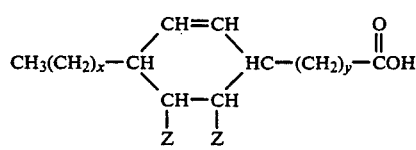

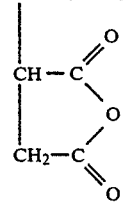

-continued

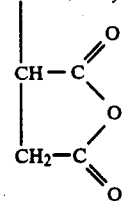

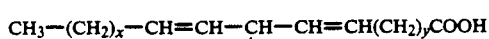

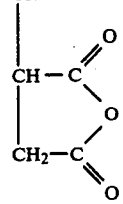

and

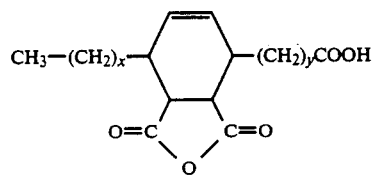

wherein x and y are integers from 3 to 9, x and y together equal 10–14, at least one Z is a carboxylic acid group and any remaining Z is hydrogen, the improvement comprising cooling the amine condensate to about 150° C. and further reacting the amine condensate at a temperature of about 220° C. to about 250° C. with a member of the group consisting of an acetic anhydride, an aromatic mono- and dicarboxylic acid, and its corresponding anhydride.

2. The slurry of claim 1 wherein the aromatic anhydride is phthalic anhydride.

3. The slurry of claim 1 wherein the slurry exhibits a reduced cure time over slurries with conventional emulsifiers at a temperature below 75° F.

4. In a cationic aqueous bituminous emulsion-aggregate slurry formed iwth cationic emulsions prepared by emulsifying bitumen in water with a cation-active emulsifier which is an amine condensate product of the reaction at a temperature of from about 30° C. to about 250° C., of about 2 moles of a polyalkylene amine with about 1 mole of a member selected from the group consisting of polycarboxylic acids and anhydrides of the following general formulae

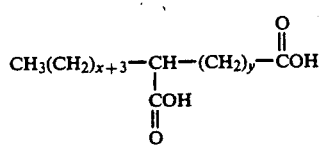

or

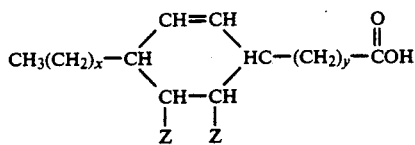

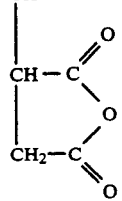

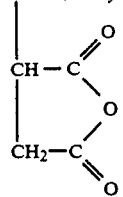

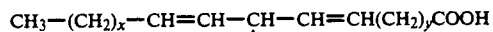

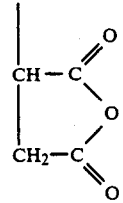

and

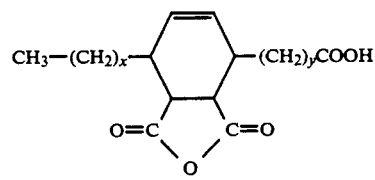

wherein x and y are integers from 3 to 9, x and y together equal 10–14, at least one Z is a carboxylic acid group and any remaining Z is hydrogen, the improvement comprising cooling the amine condensate to about 150° C. and further reacting the amine condensate at a temperature of about 220° C. to about 250° C. with organic carbonates.

5. The slurry of claim 4 wherein the organic carbonate is propylene carbonate.

6. The slurry of claim 5 wherein the slurry exhibits a reduced cure time over slurries with conventional emulsifiers at a temperature below 75° F.

* * * * *

UNITED STATES PATENT AND TRADEMARK OFFICE
CERTIFICATE OF CORRECTION

PATENT NO. : 5,034,060

DATED : July 23, 1991

INVENTOR(S) : Peter Schilling et al.

It is certified that error appears in the above-identified patent and that said Letters Patent is hereby corrected as shown below:

In column 4, line 23, before A, delete "p".

In column 6, line 31, delete "$R_1HN(CH_2)_xY(CH_2)NH_2$" and substitute therefor --$R_1HN(CH_2)_xY(CH_2)_zNH_2$--.

In column 6, line 54, before aggregate, insert --modification will determine the curing rate of the emulsion--.

In column 7, line 29, delete "$CH_3(CH_2)_5$" and substitute therefor --$CH_3(CH_2)_2$--.

In column 7, line 42, delete "asphalts" and substitute therefor --asphalt--.

In column 8, line 23, after to, insert --give asphalt emulsions of brown color and creamy texture. Prior to--.

In column 9, line 41, after fatty acids, insert --various sources, may be also co-reacted. An example of this type--.

In column 10, between lines 57 and 58, insert --Emulsifier K--.

UNITED STATES PATENT AND TRADEMARK OFFICE
CERTIFICATE OF CORRECTION

PATENT NO. : 5,034,060

DATED : July 23, 1991

INVENTOR(S) : Peter Schilling et al.

It is certified that error appears in the above-identified patent and that said Letters Patent is hereby corrected as shown below:

In column 10, line 68, delete "Exxon" and substitute therefor --Exxon®--.

In column 11, line 43, delete "1/4" and substitute therefor --1/4"--.

In Claim 4, column 13, line 47, delete "iwth" and substitute therefor --with--.

Signed and Sealed this

Second Day of November, 1993

Attest:

BRUCE LEHMAN

Attesting Officer

Commissioner of Patents and Trademarks